(12) United States Patent
Kwak et al.

(10) Patent No.: US 11,526,183 B2
(45) Date of Patent: Dec. 13, 2022

(54) TECHNIQUE FOR CONTROLLING EQUIPMENT BASED ON BIOMETRIC INFORMATION

(71) Applicant: Samsung Electronics Co., Ltd., Suwon-si (KR)

(72) Inventors: Byeong-Hoon Kwak, Uiwang-si (KR); Chang-Hyun Lee, Suwon-si (KR); Jae-Ho Jung, Yongin-si (KR); Yang-Wook Kim, Hwaseong-si (KR); Yong-Chan Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 512 days.

(21) Appl. No.: 16/598,322

(22) Filed: Oct. 10, 2019

(65) Prior Publication Data

US 2020/0057460 A1 Feb. 20, 2020

Related U.S. Application Data

(63) Continuation of application No. 15/773,358, filed as application No. PCT/KR2016/014463 on Dec. 9, 2016, now Pat. No. 10,466,726.

(30) Foreign Application Priority Data

Dec. 9, 2015 (KR) .......................... 10-2015-0175124

(51) Int. Cl.
  *G05D 23/19* (2006.01)
  *G06F 3/01* (2006.01)
  (Continued)

(52) U.S. Cl.
  CPC ........... *G05D 23/1919* (2013.01); *A61B 5/01* (2013.01); *A61B 5/02405* (2013.01);
  (Continued)

(58) Field of Classification Search
  CPC ............... G06F 3/01; G06F 3/015; G06F 3/16
  (Continued)

(56) References Cited

U.S. PATENT DOCUMENTS

2002/0072683 A1   6/2002   Schroeppel et al.
2006/0142968 A1   6/2006   Han et al.
(Continued)

FOREIGN PATENT DOCUMENTS

CN   103929662 A   7/2014
CN   104207755 A   12/2014
(Continued)

OTHER PUBLICATIONS

European Search Report dated Oct. 22, 2018; European Appln_ No. 16873392.1-121613376343.

(Continued)

*Primary Examiner* — Calvin C Ma
(74) *Attorney, Agent, or Firm* — Jefferson IP Law, LLP

(57) ABSTRACT

This disclosure relates to technologies for a sensor network, machine-to-machine (M2M) communication, machine type communication (MTC), and Internet of Things (IoT). This disclosure can be utilized in intelligent services based on the above technologies, such as smart homes, smart buildings, smart cities, smart cars or connected cars, health care, digital education, retail sales, security and safety related services, etc. This disclosure relates to a method for generating an instruction for controlling equipment on the basis of biometric information, comprising: a step of obtaining at least one biometric information; a step of determining whether to calculate a calorific value by using stored biometric information and the obtained biometric information, and calculating the calorific value by using the stored biometric information and the obtained biometric information according to the determined result; and generating an instruction (Continued)

for controlling the equipment on the basis of the calculated calorific value.

15 Claims, 11 Drawing Sheets

(51) Int. Cl.
    *G06F 3/16* (2006.01)
    *G16H 40/63* (2018.01)
    *G16H 50/20* (2018.01)
    *F24F 11/50* (2018.01)
    *A61B 5/01* (2006.01)
    *A61B 5/024* (2006.01)
    *A61B 5/0533* (2021.01)
    *A61B 5/00* (2006.01)
    *G16H 10/60* (2018.01)
    *F24F 110/10* (2018.01)

(52) U.S. Cl.
    CPC .......... *A61B 5/0533* (2013.01); *A61B 5/7405* (2013.01); *A61B 5/746* (2013.01); *F24F 11/50* (2018.01); *G05D 23/19* (2013.01); *G06F 3/01* (2013.01); *G06F 3/015* (2013.01); *G06F 3/16* (2013.01); *G16H 40/63* (2018.01); *G16H 50/20* (2018.01); *F24F 2110/10* (2018.01); *G05B 2219/2614* (2013.01); *G06F 2203/011* (2013.01); *G16H 10/60* (2018.01)

(58) Field of Classification Search
    USPC ..................................... 345/173–174; 702/19
    See application file for complete search history.

(56) References Cited

U.S. PATENT DOCUMENTS

| | | |
|---|---|---|
| 2009/0150178 A1 | 6/2009 | Sutton et al. |
| 2010/0016741 A1 | 1/2010 | Mix et al. |
| 2014/0201122 A1 | 7/2014 | Park |
| 2014/0275852 A1 | 9/2014 | Hong et al. |
| 2015/0150516 A1* | 6/2015 | Tochikubo ............ A61B 5/1118 600/301 |
| 2015/0156529 A1* | 6/2015 | Peterson ............ H04N 21/6582 725/12 |
| 2015/0177748 A1 | 6/2015 | Veh |
| 2015/0222450 A1 | 8/2015 | Ko et al. |
| 2016/0339300 A1 | 11/2016 | Todasco |
| 2020/0046301 A1* | 2/2020 | Adachi ................... G06F 3/015 |

FOREIGN PATENT DOCUMENTS

| | | |
|---|---|---|
| EP | 0 944 411 B1 | 4/2001 |
| JP | H07-103544 A | 4/1995 |
| JP | 2001-505441 A | 4/2001 |
| JP | 2005-128976 A | 5/2005 |
| JP | 2008-232467 A | 10/2008 |
| JP | 2010-255863 A | 11/2010 |
| JP | 2012-159250 A | 8/2012 |
| JP | 2012-235920 A | 12/2012 |
| JP | 2014-050451 A | 3/2014 |
| KR | 10-2006-0076829 A | 7/2006 |
| WO | 2015/108805 A1 | 7/2015 |

OTHER PUBLICATIONS

Chinese Office Action with English translation dated Jul. 24, 2020; Chinese Appln. No. 201680070665.7.
Japanese Office Action with English translation dated Dec. 1, 2020; Japanese Patent Application No. 2018-529147.
Japanese Office Action with English translation dated Jul. 6, 2021; Japanese Patent Application No. 2018-529147.
Japanese Office Action with English translation dated Mar. 8, 2022; Japanese Appln. No. 2018-529147.

* cited by examiner

EMOTIONAL STATE: NORMAL

PULSE WAVE

SKIN TEMPERATURE

GSR

BRAIN WAVE

EMOTIONAL STATE: SAD

PULSE WAVE

SKIN TEMPERATURE

GSR

BRAIN WAVE

EMOTIONAL STATE: FEARFUL

PULSE WAVE

SKIN TEMPERATURE

GSR

BRAIN WAVE

EMOTIONAL STATE: HAPPY

PULSE WAVE

SKIN TEMPERATURE

GSR

BRAIN WAVE

TECHNIQUE FOR CONTROLLING EQUIPMENT BASED ON BIOMETRIC INFORMATION

CROSS-REFERENCE TO RELATED APPLICATION(S)

This application is a continuation application of prior application Ser. No. 15/773,358, filed on May 3, 2018, and was based on and claimed priority 371 of an International application number PCT/KR2016/014463, filed on Dec. 9, 2016 which is based on and claimed priority under 35 U.S.C § 119(a) of a Korean patent application number 10-2015-0175124, filed on Dec. 9, 2015, in the Korean Intellectual Property Office, the disclosure of which is incorporated by reference herein in its entirety.

TECHNICAL FIELD

The disclosure relates to schemes for controlling equipment using biometric signals, and more particularly, to methods and devices for controlling, by a controlling apparatus, external equipment based on biometric signals.

BACKGROUND ART

The Internet is evolving from the human-centered connection network by which humans create and consume information to the Internet of Things (IoT) network by which information is communicated and processed between things or other distributed components. The Internet of Everything (IoE) technology may be an example of a combination of the Big data processing technology and the IoT technology through, e.g., a connection with a cloud server.

To implement the IoT, technology elements, such as a sensing technology, wired/wireless communication and network infra, service interface technology, and a security technology, are required. There is a recent ongoing research for inter-object connection technologies, such as the sensor network, Machine-to-Machine (M2M), or the Machine-Type Communication (MTC).

In the IoT environment may be offered intelligent Internet Technology (IT) services that collect and analyze the data generated by the things connected with one another to create human life a new value. The IoT may have various applications, such as the smart home, smart building, smart city, smart car or connected car, smart grid, health-care, or smart appliance industry, or state-of-art medical services, through conversion or integration of existing IT technologies and various industries.

There are ongoing research efforts to automatically control electronic equipment such as air conditioners based on users' state information.

For example, there are being proposed methods for automatically controlling the temperature based on the user's state information such as the temperature she feels. As per such methods, e.g., an air conditioner measures the user's apparent temperature and performs temperature control as per a predetermined rule on the measured apparent temperature.

However, since, although apparent temperature is a value calculated by a sort of formula, the temperature perceived by humans differs person to person, there cannot exist a single apparent temperature that may apply commonly to all people. Further, even at the same apparent temperature, the user may want the temperature to change in different ways (e.g., temperature up or down) depending on the user's conditions (e.g., tired or excited).

If the temperature is adjusted simply as preset at the same apparent temperature, then it would not be the way the user actually wishes. That is, how the user feels about the temperature may be subjective, and the user may want the temperature to be controlled in different ways depending on his surrounding or biometric conditions even in the same physical environment.

Thus, a need exists for a scheme capable of using state information, which may differ person to person even in the same environment, in controlling external equipment.

DETAILED DESCRIPTION OF THE INVENTION

Technical Problem

According to the disclosure, there is provided a scheme capable of controlling an equipment by determining whether the equipment needs to be controlled in the situation based on the user's biometric information.

According to the disclosure, there is provided a scheme capable of properly determining the way in which the user actually wants the equipment to be controlled when the equipment needs to be controlled.

According to the disclosure, there is provided a scheme capable of periodically measuring the user's state information and steadily reflecting the measured state information onto controlling the equipment.

According to the disclosure, there is provided a scheme for adjusting temperature by grasping whether a calorific value needs to be calculated based on the user's biometric signal, and if needed, properly determining the way and degree of changing the temperature as required.

According to the disclosure, there is provided a scheme capable of properly determining a personalized state according to a change in the physical environment, a change in the user's condition, or a change in the biometric condition.

According to the disclosure, there is provided a scheme for more precisely determining a temperature change the user desires by measuring the user's actual calorific value, not rather than statistical estimation which is centered on the physical activity.

According to the disclosure, there is provided a scheme capable of periodically measuring the user's state information and steadily reflecting the measured state information onto changing temperature.

Technical Solution

According to the disclosure, there is proposed a method for generating a command to control an equipment based on biometric information, comprising obtaining at least one piece of biometric information, determining whether to calculate a calorific value using stored biometric information and the obtained biometric information and calculating the calorific value using the stored biometric information and the obtained biometric information according to a result of the determination, and generating a command to control the equipment based on the calculated calorific value.

According to the disclosure, there is proposed an apparatus configured to generate a command to control an external equipment based on biometric information, the apparatus comprising a sensor unit configured to obtain at least one piece of biometric information, and a controller configured to determine whether to calculate a calorific value using stored biometric information and the obtained biometric information, calculate the calorific value using the stored biometric information and the obtained biometric information, and generate a command to control the external equipment based on the calculated calorific value.

According to the disclosure, there is proposed an apparatus configured to generate a command to control an external equipment based on biometric information, the apparatus comprising a memory configured to store prior biometric information, a communication unit configured to receive at least one piece of biometric information from an ambient sensor, and a controller configured to determine whether to calculate a calorific value using the stored biometric information and the received biometric information, calculate the calorific value using the stored biometric information and the received biometric information, and generate a command to control the external equipment based on the calculated calorific value.

Advantageous Effects

According to the disclosure, the user device may measure the user's state and determine, on its own, whether the calorific value needs to be calculated and may determine an operation of the external equipment appropriate for the user's state.

According to the disclosure, the apparatus controlling the equipment may sense an emotional state from the user's biometric information and use the emotional change in determining whether and how to control the equipment.

According to the disclosure, the apparatus controlling the equipment may sense the user's emotional change and trigger the operation of calculating the calorific value as the change occurs and determine an accurate and proper way to adjust the temperature based on the user's actual calorific value.

According to the disclosure, there is provided a personalized temperature adjusting scheme that may steadily reflect the user's emotional changes onto controlling the temperature by periodically measuring the user's state information.

MODE FOR CARRYING OUT THE INVENTION

Hereinafter, embodiments of the disclosure are described in detail with reference to the accompanying drawings. When determined to make the subject matter of the disclosure unclear, the detailed of the known functions or configurations may be skipped. The terms as used herein are defined considering the functions in the disclosure and may be replaced with other terms according to the intention or practice of the user or operator. Therefore, the terms should be defined based on the overall disclosure.

Before detailing the disclosure, some terms as used herein may be interpreted as follows, for example. However, it should be noted that the disclosure is not limited thereto.

Apparatus is an entity to perform the operation of controlling equipment. Accordingly, apparatus may also be referred to as a controlling apparatus. The apparatus itself may measure the user's biometric information or may receive biometric information measured by a wearable device. The apparatus may generate commands to control the equipment using the biometric information and transfer the commands to the equipment. The apparatus may be a terminal the user carries or a wearable device the user wears or may be a car navigation wheel, seat, handle, or indoor camera that the user contacts, or an external device (such as a home gateway or cloud server) that communicates with the wearable device.

Equipment is an object controlled by the apparatus. The equipment may include the apparatus but may also be implemented as a separate device from the apparatus. Thus, the equipment may also be referred to as external equipment or controlled apparatus. The equipment means all kinds of apparatuses controlled by the controlling apparatus. For example, the equipment may be an air conditioner or heater for adjusting the air temperature, a humidifier or dehumidifier for adjusting the humidity, an audio player for outputting music, a car (including an air conditioner, heating lines, and ventilation seat), various fitness equipment, or a messaging server that sends out messages to the user.

Biometric information means all types of information measured from an organism. Particularly in this disclosure, the biometric information may be at least one of heart rate (HR)-related information, electroencephalogram (EEG)-related information, galvanic skin response (GSR)-related information, breathing time or skin temperature information.

A scheme according to the disclosure may include measuring biometric information about a user, determining whether to calculate the calorific value generated from the user based on the measured biometric information, where the calorific value is required to be calculated, measuring the calorific value, determining an operation to be performed by the equipment based on the calorific value, and generating a command. As an example, determining whether to calculate the calorific value may include determining a variation in the user's emotion.

Figure 1:
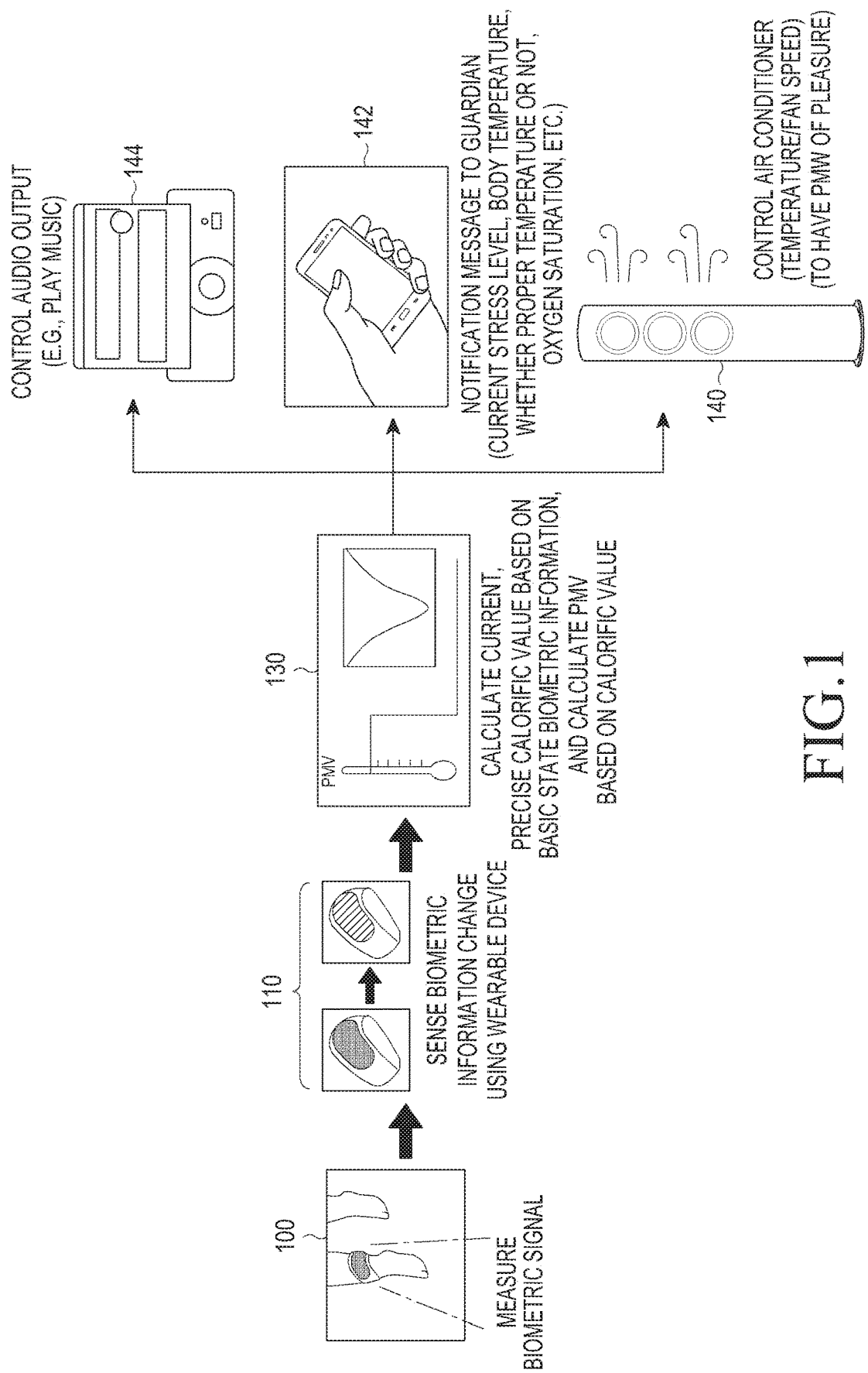
FIG. 1 is a view illustrating an example of a scenario to which an equipment control scheme is applicable according to the disclosure.

FIG. 1 is a view illustrating an example of a scenario to which an equipment control scheme is applicable according to the disclosure.

A wearable device, e.g., an armband, may be put on in contact with the user's skin. The wearable device may measure (or obtain) and store information obtainable through a contacting sensor, i.e., heart rate, galvanic skin response (GSR), EEG, skin temperature, breathing time, or other biometric information (100). Alternatively, a contactless sensor such as a camera, an infrared (IR) camera, or a thermal imaging camera may be used to obtain biometric information. For example, the camera may be used to analyze the user's facial expressions or behavior, the IR camera may measure the movement or expansion of the user's pupil or the degree of opening or closing the eyelid, and the thermal imaging camera may be used to measure the user's actual body temperature.

The biometric information measured by the wearable device or various cameras may be used to determine various additional information. For example, the heart rate information may be used to determine the user's stress, excitement, or whether she has a cardiovascular disease. The EEG information may be used to determine a brain disease, such as dementia, measure the user's concentration, or determine the user's emotional change. The GSR and skin temperature may be used to determine the user's emotional change, stress, or excitement. The breathing time information may be used to determine whether she has a cardiovascular disease or the user's excitement. Information about the user's facial expression or pupil movement which may be obtained through the camera may also be used to determine the user's emotional change or excitement.

Everyday biometric information may differ from user to user. Accordingly, adopting particular biometric information values as criteria for controlling the equipment would not satisfy users with different biometric information characteristics. Thus, a scheme according to the disclosure senses the user's state change (i.e., emotional change) based on a change in the biometric information and determines whether to control the equipment based on the state change.

For example, a controlling apparatus (e.g., the wearable device) for controlling the equipment may determine whether it is needed to control the equipment using the obtained biometric information (measured in step 100) and biometric information previously stored (110). Specifically, the controlling apparatus may determine whether to calculate the user's calorific value using the obtained biometric information and the stored biometric information. By doing so, the controlling apparatus may more precisely determine whether the user's current state requires that the equipment be controlled (i.e., the state of her emotion having been changed). Here, the stored biometric information means biometric information measured and stored before step 100. The controlling apparatus may be the above-mentioned armband (of step 100), a hair band, smart glasses or other wearable devices, a camera, an IR camera, or a thermal imaging camera. Further, the controlling apparatus may be the user's smartphone or a separate apparatus such as a home gateway or cloud server which receives the measured biometric information from the wearable device.

At this time, the biometric information used by the controlling apparatus may differ depending on where the sensor contacts or the type of the wearable device. For example, the armband may use skin temperature, pulse wave, ECG, or GSR, and the hair band may use skin temperature, pulse wave, ECG, GSR, or EEG. The smart glasses may use skin temperature, pulse wave, ECG, GSR, EEG, or pupil movement. The smartphone may use voice information it gathers or use biometric information measured by another wearable device connected with the smartphone. Further, biometric information measured by such a wearable device as smart clothing or an insertable device (e.g., an earphone or ear set) may be used to control the equipment. Further, the separate device such as a home gateway or cloud server may use information measured by the user's wearable device, smartphone, or other sensors installed in the indoor environment or biometric information measured at the outside (e.g., measured in a hospital). Devices used to determine the user's emotional change according to the disclosure are not limited to wearable devices. For example, the controlling apparatus may estimate the users' behavior pattern and emotional change using a camera equipped in a television (TV) or air conditioner or may estimate the user's emotional change based on music information that is being played on a home theater or content information that the user is viewing on the TV.

When it is determined that the equipment needs to be controlled, if the equipment is controlled as per a predetermined rule but without determining the way the user actually wants the equipment to be controlled in, then the equipment would not be controlled in the way the user truly desires. Thus, the scheme according to the disclosure generates state information (e.g., the calorific value or apparent temperature) necessary for controlling the equipment using the biometric information and determines how to control the equipment according to the state information. For example, upon determining to calculate the calorific value, the controlling apparatus may calculate the calorific value (M: metabolism) using the pre-stored biometric information and the obtained biometric information and calculate the user's actual apparent temperature based on the calorific value (130). For example, the apparent temperature may be calculated as a predicted mean vote (PMV). The PMV may be a value ranging from −3 to 3. When the PMV is a value not less than −0.5 and not more than 0.5, the user may be determined to be in a pleasant state where the equipment need not control.

Accordingly, the controlling apparatus may generate a command to control the operation of the equipment based on the state information and deliver the command.

For example, if the calculated PMV is a value less than −0.5 or more than 0.5, the controlling apparatus may generate a command to control the equipment and deliver the command to the equipment. For example, the controlling apparatus may transmit a command to change the set temperature or a command to change the fan speed to an air conditioner which controls the air temperature. At this time, the controlling apparatus may determine what control command it would issue considering various factors (e.g., power, number of users, etc.). For example, where the current temperature is sufficiently low as compared with the outside temperature so that the power consumption for lowering the set temperature is smaller than the power consumption for speeding up the fan, the controlling apparatus may adjust the fan speed to be high. As another example, upon determining that a number of users are in the room and they are unhappy about the current temperature, the controlling apparatus may adjust the set temperature rather than adjusting the fan speed.

As another example, the controlling apparatus may transmit, to a messaging server, a command to enable it to send a notification message indicating that the user is unpleasant to the user (e.g., a baby or patient) or another user (e.g., his guardian) (142).

As another example, the controlling apparatus may transmit, to the equipment, e.g., an audio component, a command to enable it to play music fitting the user's state change (144).

Figure 2:
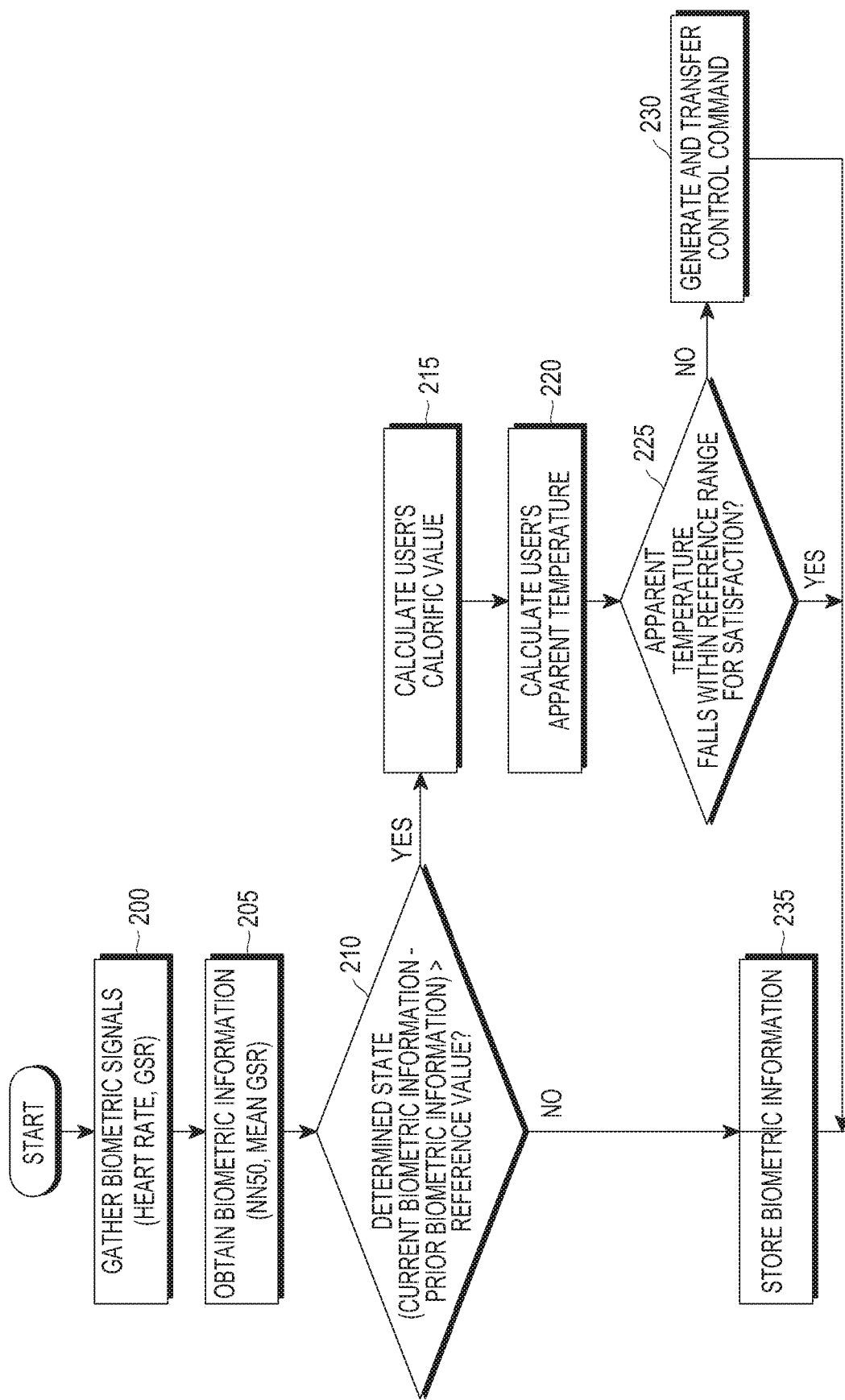
FIG. 2 is a view illustrating an example of an equipment control method by a controlling apparatus according to the disclosure.
Figure 3A:
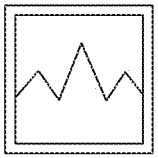
FIGS. 3A, 3B, 3C and 3D are views illustrating an example of a biometric signal measured where a user's emotional state is normal.
Figure 3A:
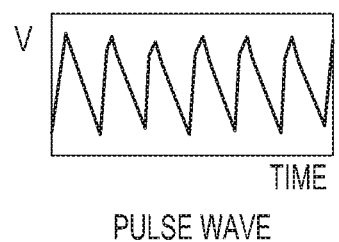
Figure 3B:
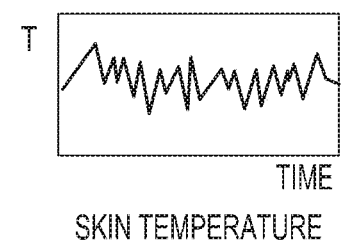
Figure 3C:
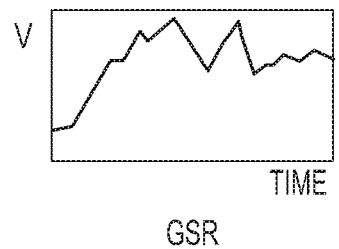
Figure 3D:
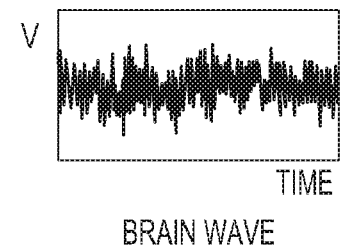
Figure 4A:
FIGS. 4A, 4B, 4C and 4D are views illustrating an example of a biometric signal measured where a user's emotional state is sad.
Figure 4A:
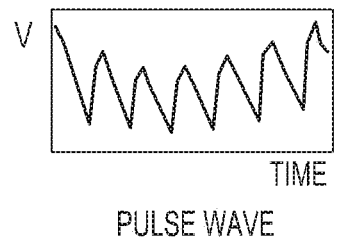
Figure 4B:
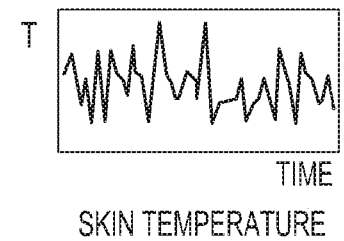
Figure 4C:
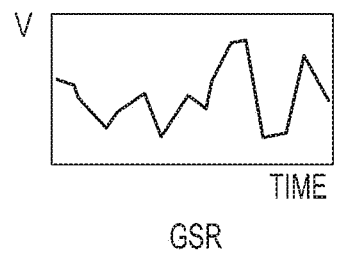
Figure 4D:
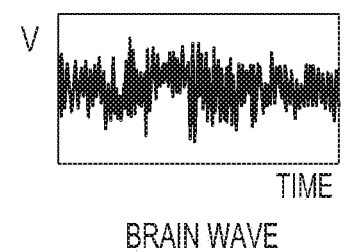
Figure 5A:
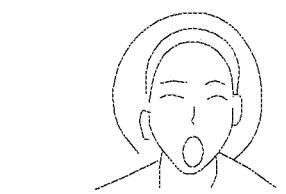
FIGS. 5A, 5B, 5C and 5D are views illustrating an example of a biometric signal measured where a user's emotional state is fearful.
Figure 5A:
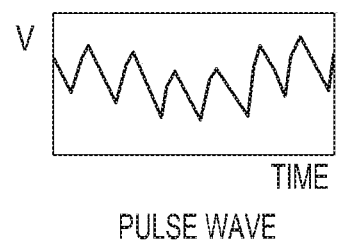
Figure 5B:
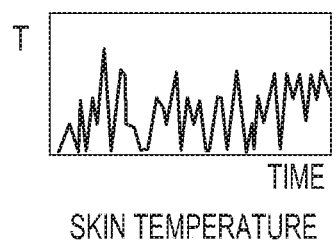
Figure 5C:
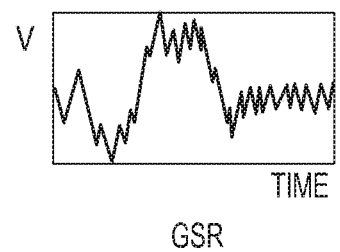
Figure 5D:
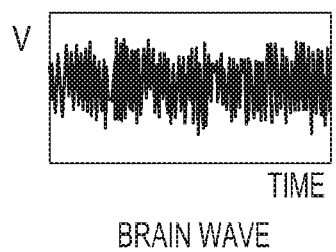
Figure 6A:
FIGS. 6A, 6B, 6C and 6D are views illustrating an example of a biometric signal measured where a user's emotional state is happy.
Figure 6A:
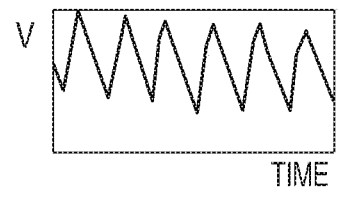
Figure 6B:
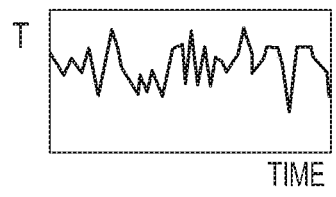
Figure 6C:
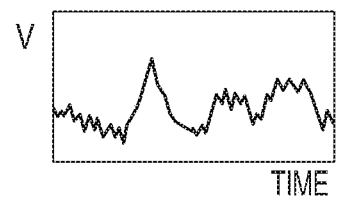
Figure 6D:
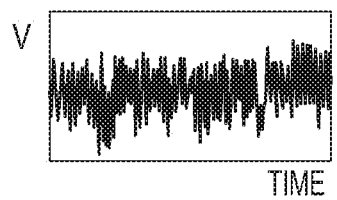

FIG. 2 is a view illustrating an example of an equipment control method by a controlling apparatus according to the disclosure.

The controlling apparatus may measure the user's biometric signal (200). Selectively, the measurement of the biometric signal may be performed not by the controlling apparatus but by another apparatus. Examples of the biometric signal include heart rate (HR), pulse transmit time (PTT), GSR, skin temperature, breathing time, or brain waves (on the frontal lube or parietal lobe). The table below represents examples of the biometric signal, where the biometric signal is measured, and sensors capable of the measurement.

TABLE 1

| biometric signal-biometric information | | sensor | portion measured |
|---|---|---|---|
| heart rate | Mean HRV SDNN RMSSD NN50 HL/LF | ECG sensor, PPG sensor (skin-attaching type) | chest, limb terminal |
| pulse transmit time | mean standard deviation | PPG sensor (ring, watch) | limb terminal |
| breathing time | mean standard deviation zero-crossing ratio | | |
| skin temperature | mean standard deviation | temperature sensor (skin-attaching type) | eardrum, wrist |
| galvanic skin response | mean standard deviation | GSR sensor (skin-attaching type) | anywhere in body |
| brain wave on frontal lube | δ wave θ wave α wave β wave γ wave | EEG sensor (patch type) | head, particular portion |
| brain wave on parietal lobe | δ wave θ wave α wave β wave γ wave | | |

For example, where the biometric signal is the heart rate, a skin-attaching electrocardiograph (ECG) sensor or photoplethysmogram (PPG) sensor may measure (or obtain) the mean heart rate, heart rate variability (HRV), standard deviation of the normal to normal interval (SDNN), square root of the mean squared differences of successive normal to normal intervals (RMSSD), normal to normal interval 50 (NN50) (a ratio of continuous intervals with a variation of 50 ms or more to all the normal to normal intervals), high frequency (HF), or low frequency (LF). As another example, where the biometric signal is the GSR, a GSR sensor may measure (or obtain) biometric information such as mean GSR or zero crossing rate. As another example, where the biometric signal is the brain wave, a patch-type EEG sensor may measure (or obtain) the EEG on the frontal lube or parietal lobe. The brain waves may be delta (δ) waves, theta (θ) waves, alpha (α) waves, beta (β) waves, or gamma (γ) waves.

The controlling apparatus may obtain at least one piece of biometric information (such as, e.g., NN50 or mean GSR) by analyzing the measured biometric signal (205).

The controlling apparatus may determine whether the user is currently in the state of requiring that the calorific value be calculated to control the equipment using the obtained biometric signal (210). For example, where a variation ratio of the value indicated by the obtained biometric information to the value indicated by the pre-stored biometric information is a reference value (threshold) or more, the controlling apparatus may determine to calculate the calorific value. That is, the scheme of the disclosure uses the fact that a variation in the biometric information reflects the user's emotional change at a high accuracy.

FIGS. 3A, 3B, 3C and 3D are views illustrating an example of a biometric signal measured where a user's emotional state is normal.

In FIGS. 3A, 3B, 3C and 3D, the horizontal axis of the biometric signal denotes the time, and the vertical axis denotes the voltage [V], temperature [T, in degrees Fahrenheit], voltage [V], and voltage [V] for pulse wave, skin temperature, GSR, and EEG, respectively. When the user's emotional state is relatively normal, it can be shown that the pulse wave is intermittently fluctuated, and the amplitude of the GSR is not large.

FIGS. 4A, 4B, 4C and 4D are views illustrating an example of a biometric signal measured where a user's emotional state is sad.

In FIGS. 4A, 4B, 4C and 4D, the horizontal axis of the biometric signal denotes the time, and the vertical axis denotes the voltage [V], temperature [T, in degrees Fahrenheit], voltage [V], and voltage [V] for pulse wave, skin temperature, GSR, and EEG, respectively. When the user's emotional state is relatively sad, it can be shown that the pulse wave is frequently fluctuated, and the amplitude of the GSR is not large.

FIGS. 5A, 5B, 5C and 5D are views illustrating an example of a biometric signal measured where a user's emotional state is fearful.

In FIGS. 5A, 5B, 5C and 5D, the horizontal axis of the biometric signal denotes the time, and the vertical axis denotes the voltage [V], temperature [T, in degrees Fahrenheit], voltage [V], and voltage [V] for pulse wave, skin temperature, GSR, and EEG, respectively. When the user's emotional state is relatively fearful, it can be shown that the pulse wave is intermittently fluctuated, and the amplitude of the GSR is large.

FIGS. 6A, 6B, 6C and 6D are views illustrating an example of a biometric signal measured where a user's emotional state is happy.

In FIGS. 6A, 6B, 6C and 6D, the horizontal axis of the biometric signal denotes the time, and the vertical axis denotes the voltage [V], temperature [T, in degrees Fahrenheit], voltage [V], and voltage [V] for pulse wave, skin temperature, GSR, and EEG, respectively. When the user's emotional state is relatively happy, it can be shown that the pulse wave is significantly fluctuated, and the amplitude of the GSR is not large.

FIGS. 3A to 6D exemplify the waveforms of the pulse wave (FIG. 3A, FIG. 4A, FIG. 5A, and FIG. 6A), skin temperature (FIG. 3B, FIG. 4B, FIG. 5B, and FIG. 6B), GSR (FIG. 3C, FIG. 4C, FIG. 5C, and FIG. 6C), and EEG (FIG. 3D, FIG. 4D, FIG. 5D, and FIG. 6D) for four example emotional states (normal, sad, fearful, and happy), respectively. Generally, the heart rate slows down at no stimulus but goes up at excitement. Further, the GSR means the degree of activation of the sympathetic nervous system, and at a high emotional change, its amplitude goes up and the degree of activation increases. A tendency for brain waves is such that alpha waves, beta waves, theta waves, gamma waves, and delta waves increase when the user is stable, unstable, focusing, fretful, and sleeping, respectively.

Figure 7:
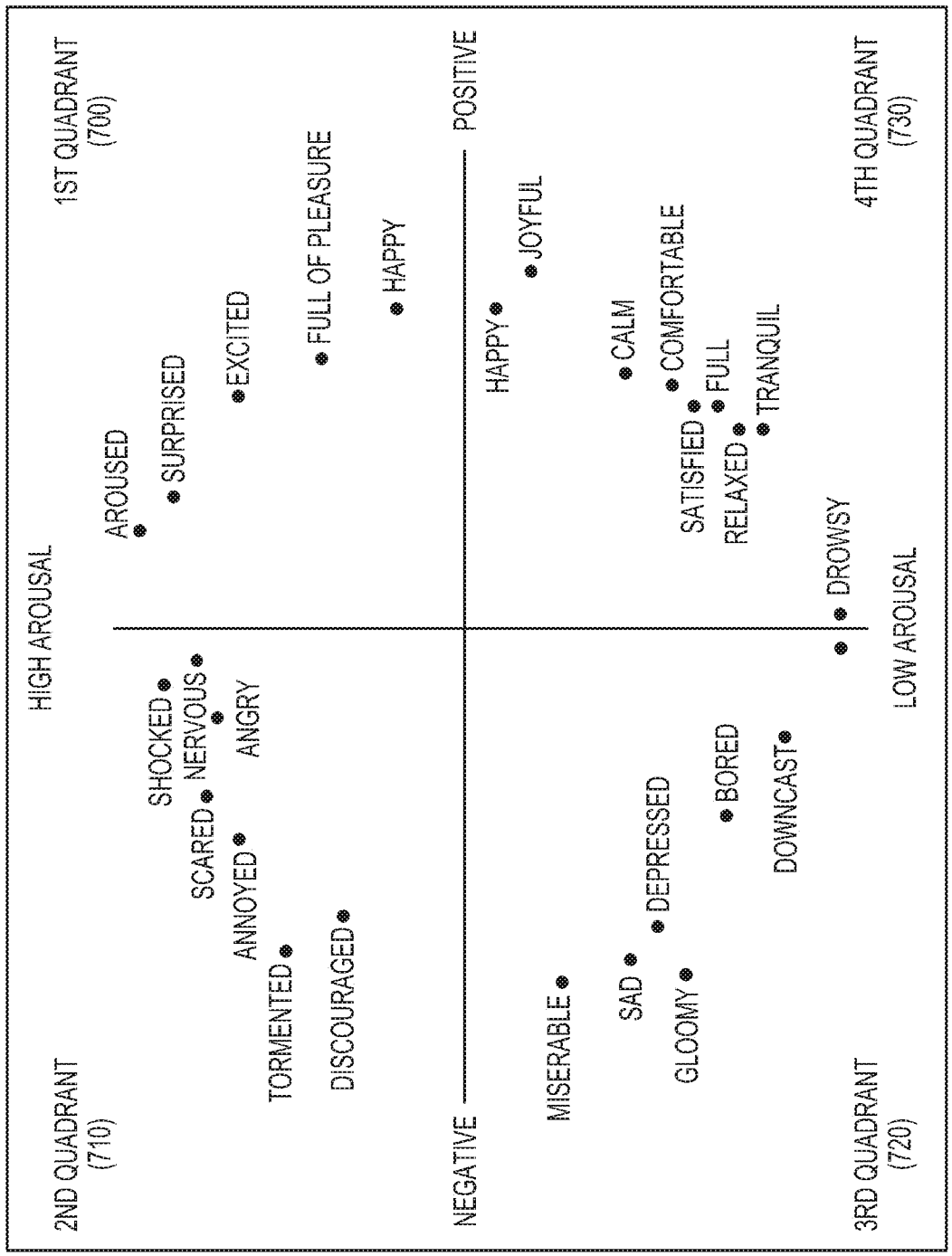
FIG. 7 is a view illustrating an example of four distinct emotional states.

FIG. 7 is a view illustrating an example of four distinct emotional states.

The first quadrant 700 on the upper and right part of FIG. 7 represents a high arousal positive emotional state (e.g., happy). The fourth quadrant 730 on the lower and right part of FIG. 7 represents a low arousal positive emotional state (e.g., tranquil). The second quadrant 710 on the upper and left part of FIG. 7 represents a high arousal negative emotional state (e.g., fearful). The third quadrant 720 on the lower and left part of FIG. 7 represents a low arousal negative emotional state (e.g., sad). The emotional states may be determined by using various pieces of biometric information individually or in combination. As the biometric information measured becomes more accurate, more biometric information is accumulated, or more types (numbers) of biometric information are combined, the determination on the emotional state becomes more accurate.

The controlling apparatus of the disclosure may determine the directivity of the emotion. Specifically, the controlling apparatus may determine that an emotional change from positive to negative, i.e., a transition from the first or fourth quadrant of FIG. 4 to the second or third quadrant, is a state change where the equipment need control. To sense a change in the emotional state, there is proposed herein a scheme of using GSR information and heart rate information. The use of the two pieces of information enables catching an emotional change with a high accuracy of about 79%.

Table 2 represents examples of changes in biometric information indicating emotional states.

TABLE 2

| emotion | | pleasant | | unpleasant | |
| --- | --- | --- | --- | --- | --- |
| | | calm (4th quadrant) | happy (1st quadrant) | fearful (2nd quadrant) | sad (3rd quadrant) |
| heart rate | HRV | stable | stable | unstable | unstable |
| | NN50 | low | low | high | low |
| | pulse transmit time | slow | fast | fast | slow |
| galvanic skin response | degree of activation | low | active | active | low |
| | amplitude | weak | strong | strong | weak |

Referring to Table 2, the emotional state may be determined. For example, where a change of the current HRV relative to an HRV previously stored is 20% or more, the HRV may be determined to be unstable, and the controlling apparatus may determine that the emotional state is the fearful or sad state that may occur where the HRV is unstable. As another example, where the current NN50 value increases by 10% or more relative to an NN50 previously stored, the NN50 may be determined to be high, and the controlling apparatus may determine that the emotional state is the fearful state that may occur where the NN50 is high. As another example, where the current GSR value increases by 5% or more relative to a GSR previously stored, the degree of GSR activation may be determined to be 'active,' and the controlling apparatus may determine that the emotional state is the happy or fearful state that may occur where the degree of activation is 'active.' As another example, the controlling apparatus may determine that the current emotional state is the fearful (i.e., unpleasant) state on the second quadrant by combining all of the pieces of information, determining that the equipment needs to be controlled. Selectively, the controlling apparatus may determine that the variation in the biometric information is in proportion to the strength of the emotional change.

In step 210 above, where the variation is less than the reference value, the controlling apparatus may determine that it is not needed to control the equipment. That is, the controlling apparatus may determine that it is not needed to calculate the calorific value generated from the user. At this time, the controlling apparatus may store the measured control information (235) and perform no further operation to the next period.

In step 210 above, where the variation is not less than the reference value, the controlling apparatus may determine that it is needed to control the equipment. That is, the controlling apparatus may determine that it is needed to calculate the calorific value generated from the user. In this case, the controlling apparatus may calculate the user's actual calorific value (M: metabolism) using the measured biometric information and the pre-stored biometric information (215) and calculate the user's apparent temperature using the calculated calorific value (220). Preferably, the pre-stored biometric information is biometric information in a base state which may mean that the user feels no or little stress.

Calculating (215) the actual calorific value using the biometric information may be performed by the following equations.

$$HR = HR_0 + RM*(M-M_0) \quad \text{Equation 1}$$

$$RM = (HR_{mx} - HR_0)/(MWC - M_0) \quad \text{Equation 2}$$

$$HR_{max} = 205 - 0.62A \quad \text{Equation 3}$$

$$MWC = (41.7 - 0.22A)P^{0.666} \text{ [W/m}^2\text{] (male)}$$

$$MWC = (35.0 - 0.22A)P^{0.666} \text{ [W/m}^2\text{] (female)} \quad \text{Equation 4}$$

Here, HR is the current heart rate, and $HR_0$ is the heart rate in the base state, i.e., when the user is relaxing at a neutral temperature where it is neither hot nor cold. Here, the base state refers to a state where the user feels stable with less motion and stress. For example, $HR_0$ may be defined as the heart rate measured in the state where the state information such as HRV or pNN50 (=NN50/heart rate) is not more than a predetermined value or the heart rate measured when the stress information value inferrable from the heart rate indicats a state where the user is not stressed out. As the pNN50 decreases, the user may be determined to be not stressed out. $HR_{max}$ is the maximum heart rate at the theoretically maximum user activity, e.g., when the user runs, and an estimated value may be used as $HR_{max}$.

RM denotes a ratio at which the heart rate increases as per activities, M denotes calorific value (i.e., activity), and $M_0$ denotes calorific value at relaxation. M0 may be replaced with the basal metabolism. MWC denotes the maximum workability, and P and A denote weight and age, respectively.

Summing up the equations, it can be shown that the user's actual calorific value M is calculated using a difference between the current heart rate (i.e., biometric information) and the pre-stored heart rate as shown in the following equation.

$$M = \frac{HR - HR_0}{RM} + M_0 \quad \text{Equation 5}$$

The apparent temperature 220 calculable using the calorific value may come in various types. Such types of apparent temperatures may include not only the typical apparent temperature which is calculated considering temperature and wind speed, but also the effective temperature (ET) which also takes into account wind speed, humidity, and radiant temperature or further the standard new ET (SET) which is calculated given activity and clothing in addition to humidity and wind speed. The operative temperature which considers air temperature, activity, clothing, and wind speed, but not humidity, is a sort of apparent temperature. The scheme of the disclosure may make use of the predicted mean vote (PMV) that is determined by the following equation considering temperature, air flow (by convection current), humidity, radiant temperature, activity, and clothing, as the apparent temperature, as defined in International Organization for Standardization (ISO) 7730.

$$PMV = (0.352e^{-0.042} + 0.032)$$

$$\times [(M-W) - 0.35(43 - 0.061(M-W) - P_a)$$

$$-0.42(M-W-50) - 0.0023M(44-P_a)$$

$$-0.0114M(34 - t_{air})$$

$$-3.4 \times 10^{-8} f_{cl}\{(t_{cl}+273)^4 - (t_{mrt}+273)^4\}$$

$$-f_{cl} h_c (t_{cl} - t_{air})] \quad \text{Equation 6}$$

Here, W is the unit of external work and this is set as 0 for most of activities. $f_{cl}$ denotes the ratio of the body surface area when the user is dressed up to the body surface area when the user is naked, $t_{air}$ denotes the air temperature, $P_a$ denotes the water vapor partial pressure (unit: Pa), $t_{cl}$ is the surface temperature of the clothing, $t_{mrt}$ is the mean radiant temperature, and h-c is the convection current thermal transfer coefficient. The clothing for calculating the body surface area ratio may be determined assuming a normal way to wear as per the current mean air temperature and the season. The PMV value determined by Equation 6 may range from −3 to 3.

The controlling apparatus may determine how to control the equipment based on the calculated apparent temperature (225). For example, the apparent temperature may be calculated as the PMV value, and where the PMV value falls out of a predetermined range (e.g., −0.5<=PMV<=0.5), the controlling apparatus may generate/transmit a command to control the equipment (230), and where the PMV value falls within the predetermined range, the controlling apparatus may abstain from generating/transmitting a command to control the equipment. The equipment may be, e.g., an air conditioner. Where the PMV value falls out of the predetermined range and is positive, the controlling apparatus may generate and transmit a command to enable the air conditioner to lower the set temperature. Where the PMV value falls out of the predetermined range and is negative, the controlling apparatus may generate and transmit a command to enable the air conditioner to raise the set temperature.

Table 3 represents an example in which the controlling apparatus controls the equipment to adjust the temperature based on the PMV value.

TABLE 3

| current PMV | target PMV | set temperature | fan speed | clothing guide |
|---|---|---|---|---|
| PMV >0.5 | PMV = 0.3 | temperature down | increase fan speed | recommend thin clothing |
| PMV <−0.5 | PMV = −0.3 | temperature up | decrease fan speed | recommend thick clothing |

The controlling apparatus may generate and transmit commands to control operations (e.g., increase/decrease the air temperature, speed, direction, and humidity) a cooler, heater, humidifier, or dehumidifier to set the PMV to be within the range from −0.5 to 0.5 based on the calculated PMV value. For example, where the current PMV exceeds 0.5, the controlling apparatus may generate a control command to increase the fan speed or lower the set temperature of the air conditioner to achieve a target PMV of 0.3. As another example, where the current PMV is less than −0.5, the controlling apparatus may generate a control command to decrease the fan speed or raise the set temperature of the air conditioner to achieve a target PMV of −0.3. That is, the controlling apparatus may use, singularly or in combination, the set temperature and the fan speed in determining the type of control command.

The controlling apparatus may determine a control operation for the equipment considering external factors (e.g., cooling efficiency, power, and number of people). For example, where the indoor-outdoor temperature difference is a predetermined value or more, the controlling apparatus may determine that an additional lowering or raising of the set temperature may deteriorate the cooling/heating efficiency and may thus generate a control command to increase the fan speed. As another example, where a number of users are in the room and their emotional state is unpleasant, the controlling apparatus may generate a control command for lowering the set temperature despite a deterioration of cooling efficiency, rather than increasing the fan speed.

As another example, upon determining that the indoor temperature is sufficiently low as compared with the outdoor temperature so that it is impossible to further adjust the set temperature or to further satisfy the user, the controlling apparatus may transmit a message to advise the user to put on or take off to the user.

As another example, where a number of users are in the space, the controlling apparatus may identify whether they experience an emotional change, and where the number of users who experience an emotional change is a predetermined value or more, the controlling apparatus may determine whether it is needed to control the equipment considering the PMV or the calorific value generated from the users who caused the emotional change, and if necessary, generate a command to control the equipment.

As another example, where a number of users are in the space, the controlling apparatus may identify whether they cause an emotional change, and where only a small number of users (the number is smaller than a predetermined value) causes an emotional change, the controlling apparatus may generate a control command to enable the air blow to be oriented only to the users of the emotional change.

As another example, where a number of users are in the space, the controlling apparatus may calculate the PMV for a portion in the space using the external temperature measured by the user's wearable device and generate a control command to allow the air blow to be oriented to the portion of the space.

Selectively, the controlling apparatus may further perform the operation of storing the results (i.e., variations) of determining the state in step 210, and upon performing a next (i.e., after a predetermined time after) operation for controlling the equipment, the controlling apparatus may compare a variation in the state information with the stored variation and reflect whether the variation increases onto controlling the equipment.

Table 4 exemplifies an example of receiving a feedback for the user's emotional change based on the state information and using the emotional change in controlling the equipment.

TABLE 4

| directivity of state change | adjust control of equipment as per feedback |
|---|---|
| increase in pleasure | register currently calculated PMV as favored PMV, record temperature measurement and air flow speed |
| increase in displeasure | further control air conditioner to have ±0.5 higher PMV than target value as set |
| second increase in pleasure (second feedback) | adjust PM or $M_0$ for correcting PMV |
| second increase in displeasure (second feedback) | displeasure occurs due to external factor. Notify user |

For example, where the user's emotional change indicated by the feedback indicates pleasure up (i.e., the directivity of the state information changes and the variation increases), the controlling apparatus may further perform an operation for registering the currently calculated PMV, temperature measurement, or air flow speed as the user's favored values and use the favored values in controlling the equipment. As another user, where the user's emotional change indicated by the feedback indicates displeasure up (i.e., the directivity of the state information is maintained and the variation increases), the controlling apparatus may further control the air conditioner to have a PMV value which is ±0.5 higher than the current target PMV value.

Selectively, a predetermined time after controlling the equipment as per the feedback, the controlling apparatus may re-measure the user's emotional change (second feedback) and further use the measured emotional change in controlling the equipment. At this time, where the user's emotional change indicated by the second feedback indicates secondary pleasure up, the controlling apparatus may change $M_0$, $HR_{max}$, or RM to calculate a more proper PMV value. For example, the controlling apparatus may perform a first control so that the PMV which used to be calculated as −0.8 becomes 0.3, and then, as the first feedback received indicates more unpleasant, the controlling apparatus performs a second control by adding +0.5 so that the PMV becomes 0.8. Then, as the received second feedback indicates more pleasant, the controlling apparatus may adjust (or change) $M_0$, $HR_{max}$, or RM so that the current PMV, 0.8, becomes 0.3. At this time, the controlling apparatus may perform such adjustment (or change) by selecting, from among $M_0$, $HR_{max}$, or RM, one whose current value shows the least difference from that of the average person (corresponding to the mean state information).

Further, where the user's emotional change indicated by the second feedback indicates secondary displeasure up, the controlling apparatus may determine that such displeasure has come not from the temperature adjustment but from an external factor and generate a command to let it notify the user (e.g., by outputting a notification message on the screen or an alarm through the speaker).

For the controlling apparatus to exactly determine the apparent temperature used to control the equipment, it is critical to precisely determine the user's actual calorific value. Accordingly, for the controlling apparatus to properly control the equipment, it is required to accurately determine the heart rate in the base activity, i.e., $HR_0$, which is used to determine the calorific value.

Figure 8:
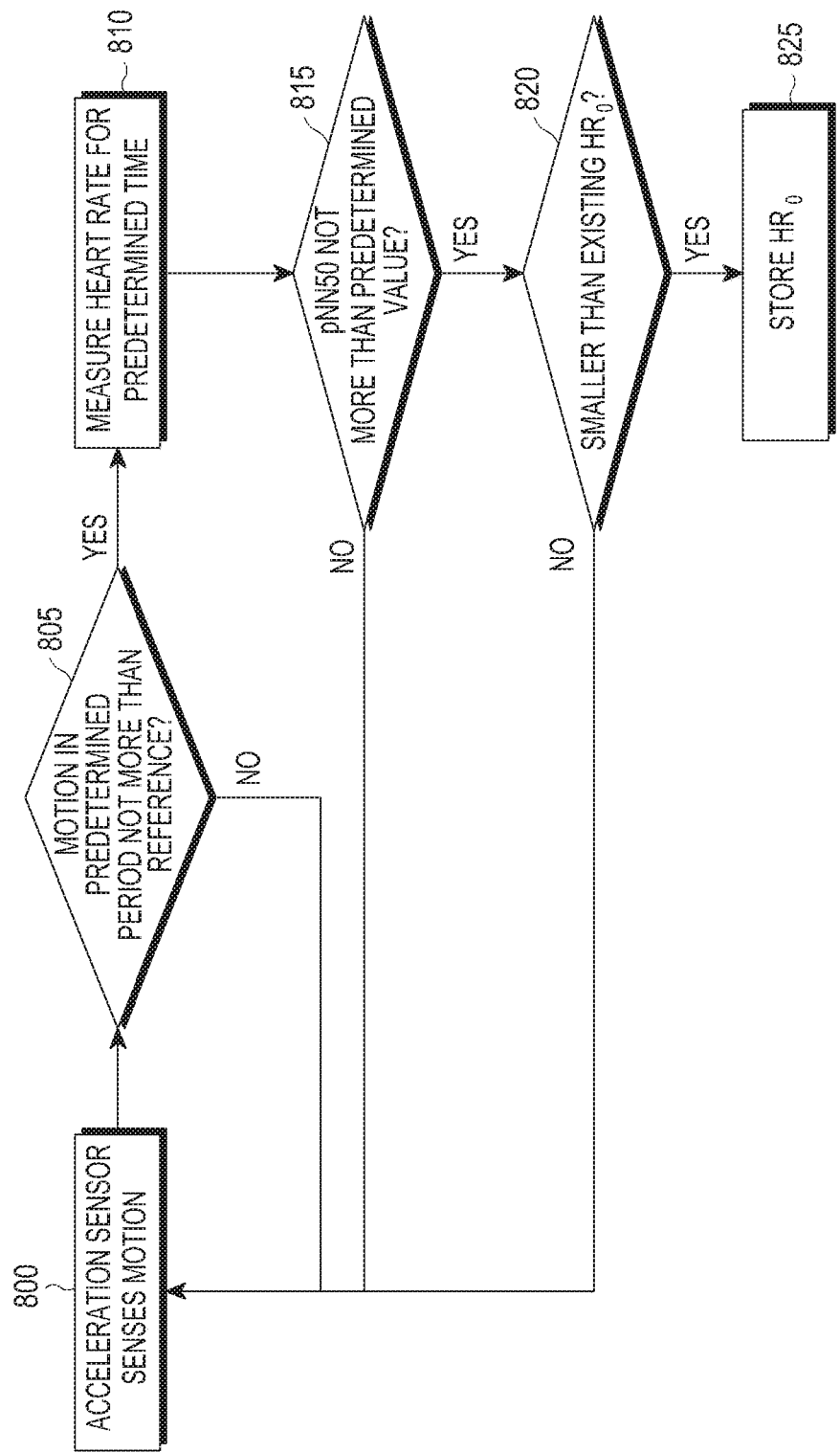
FIG. 8 is a view illustrating an example of a method for determining $HR_0$ by a controlling apparatus according to the disclosure.

FIG. 8 is a view illustrating an example of a method for determining $HR_0$ by a control device according to the disclosure.

A series of operations shown in FIG. 8 may be repeated each cycle by the controlling apparatus.

The controlling apparatus may sense its movement (i.e., the user's motion) using an acceleration sensor (or gyro sensor) (800).

The controlling apparatus may check whether the movement of the controlling apparatus during a predetermined period is a reference value or less (805). For example, the controlling apparatus may check if the value sensed by the acceleration sensor for 20 minutes is 1G (indicating that she remains still) or less.

Where the movement of the controlling apparatus during the predetermined period is the reference value or less, the controlling apparatus may measure the user's heart rate (810).

The controlling apparatus may obtain biometric information such as HRV or NN50 using the measured heart rate and check if the HRV or pNN50 is a predetermined value or less (815). Where the HRV or pNN50 which indicates the user's stress is the predetermined value or less, the controlling apparatus may determine that the user is under no or less stress. Alternatively, the controlling apparatus may also determine the no-stress state using the user's heart rate or stress information inferrable from the user's heart rate.

The controlling apparatus may compare the existing $HR_0$ with the heart rate measured in step 210, determining that it is the minimum (820).

Where the heart rate measured in step 210 is the minimum, the controlling apparatus may store the measured heart rate as the $HR_0$ value (825).

Figure 9:
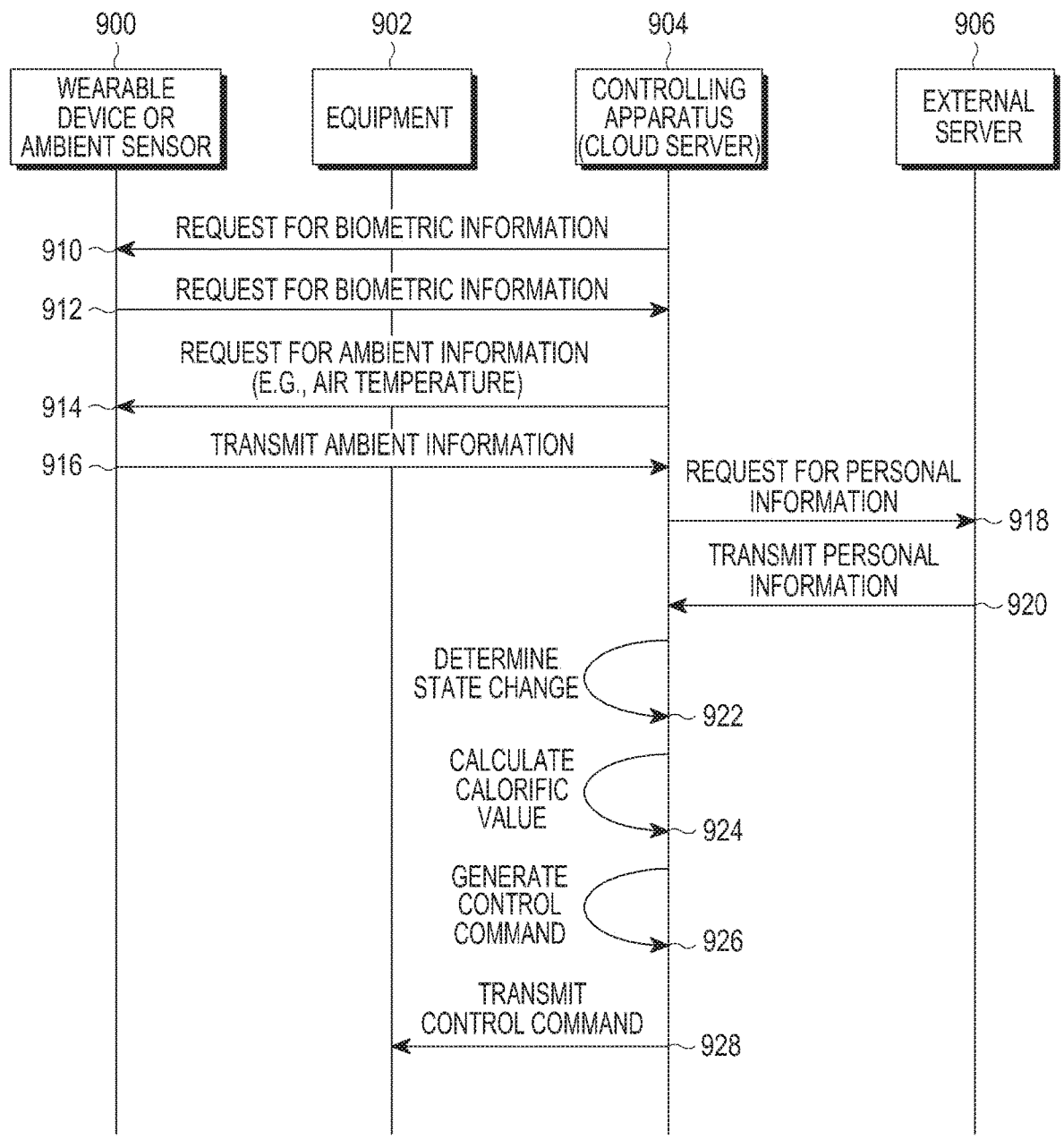
FIG. 9 is a view illustrating an example of a specific control method where a controlling apparatus is a cloud server according to the disclosure.

FIG. 9 is a view illustrating an example of a specific control method where a control device is a cloud server according to the disclosure.

A cloud server 904 may send a request for biometric information to a wearable device 900 that may be put on the user (910) and receive biometric information from the wearable device 900 (912).

Selectively, the cloud server 904 may send a request for other various pieces of information than the biometric information (914) and receive the information (916). Specifically, the cloud server 904 may also receive the user's information that is measured from an ambient sensor 900 or the user's indoor environment as well as from the wearable device 900. Examples of the user information that may be gathered from the ambient sensor may include the user's motion and facial expression information that may be gathered from, e.g., a camera, the amount of carbon dioxide in the air that may be gathered from, e.g., a gas sensor, the user's activity and action estimation information that may be gathered from, e.g., a motion sensor, and sound information that may be gathered from, e.g., a sound sensor (microphone).

At this time, the cloud server 904 may determine the user's emotional change (922) based on the user information or analyze the user's activity to determine whether it is required to calculate the calorific value (924). For example, the cloud server 904 may infer the user's emotional state from the user's temperature-related motion (e.g., continue shaking her hand to her face, put on or take off clothes, or wear a mask) that is gathered from the camera or the user's facial expression changes. Further, the cloud server 904 may calculate the calorific value generated from the user based on a change in the amount of carbon dioxide in the air which is gathered from the gas sensor and estimate the user's state change. As another example, the cloud server 904 may determine the user's emotional change and calculate the calorific value based on the user's activity information measured by the motion sensor. As another example, the cloud server 904 may determine the user's emotional change based on, e.g., the user's voice tone, whether high or low, as measured by the sound sensor.

Selectively, the cloud server may send a request for the user's personal information to another server (external server) 906 (918) and receive the user's personal information from the external server 906 (920). Examples of the user's personal information which may be gathered from the external server 906 may include the disease history, prescription records, movement capability measurement information, basal metabolism information, and the user's biometric measurement information which may be received from the hospital server.

Examples of the external server 906 may include an electronic medical record (EMR) server or a personal health record (PHR) server. Examples of the EMR may include hospital-related information such as treatment history, disease history, and prescription records, and examples of the PHR may include movement capability, basal metabolism, user biometric measurement information, maximum heart rate, and minimum heart rate. Since the treatment history may represent the user's body condition (e.g., whether she has a cold, fever, or blood flow slowdown), the cloud server 904 may use the state information in calculating the calorific value or generating control commands. As the disease history may represent the user's past disease history (whether she got surgery or suffered from poor immunity), the cloud server 904 may use the history information in calculating the calorific value or generating control commands. As the prescription records may represent information about medications prescribed, the cloud server 904 may generate commands to control the equipment to set a temperature proper for medication prescription based on the prescription records (e.g., adjust the temperature to assist in, or not to too rush, absorbing medication). The movement capability information may represent, e.g., basal metabolism, user biometric measurement information, maximum heart rate, and minimum heart rate. The cloud server 904 may calculate the user's calorific value using the movement capability information as a personalization factor in calculating, e.g., $M_0$, $HR_{max}$, or surface area.

The cloud server 904 may estimate the user's state change (922) or generate control commands (926) using the personal information. For example, the cloud server may generate a command to control the equipment based on the user's disease history obtained from the external server. That is, where the user got a cold, the cloud server may set the range of pleasure to be warmer (e.g., $-0.2<=PMV<=0.8$) than usual. The cloud server may set the range of pleasure to be warmer than usual to assist in absorbing medication based on the user's prescription records. As another example, the cloud server may calculate the user's maximum heart rate based on the user's movement capability measurement information and utilize the same in calculating the calorific value. Further, the cloud server may use the user's basal metabolism as basic information for precisely calculating the user's calorific value. The user's biometric measurement information may be used as a material index in obtaining the body surface area to calculate the user's calorific value.

The scheme according to the disclosure may also be used in taking care of infants at home.

Figure 10A:
FIGS. 10A, 10B and 10C are views illustrating an example of a scenario where a scheme of the disclosure is implemented in a home.
Figure 10B:
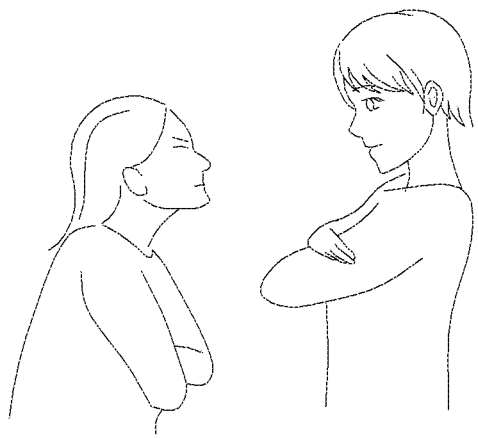
Figure 10C:

FIGS. 10A, 10B and 10C are views illustrating an example of a scenario where a scheme of the disclosure is implemented in a home.

FIG. 10A shows a hypothesis in which an infant wearing a smart band or smart clothes (i.e., a controlling apparatus) kicks off her blanket while sleeping. Upon sensing the infant's emotional change to being cranky or stressful, the controlling apparatus may measure the calorific value generated from the infant and controls the air conditioner to adjust the temperature. Where the infant's conditions does not get better within a predetermined time, the controlling apparatus may transmit a command to the messaging server to enable it to send a notification message to the infant's guardian and may also perform control to further adjust the temperature.

FIG. 10B shows a hypothesis in which an infant and an adult wear their respective smart bands or smart clothes (i.e., controlling apparatus). Where the adult's condition is pleasant but the infant is cranky or stressful, the controlling apparatus may measure the calorific value generated from the infant and command the equipment to set the temperature to more fit for the infant or to send a message to her guardian.

FIG. 10C shows a hypothesis in which an infant wearing a smart bands or smart clothes (i.e., controlling apparatus) is sick. Where the infant's condition change to being cranky or stressful is repeatedly sensed, the controlling apparatus may control the equipment to send a notification message to her guardian, but rather than controlling the temperature through the equipment.

The scheme as per the disclosure may also perform control to, e.g., increase the user's convenience or prevent a car driver' drowsy driving based on the biometric information about the driver or passengers.

Figure 11A:
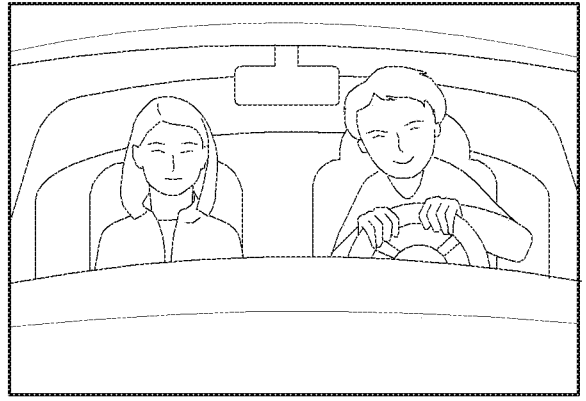
FIGS. 11A and 11B are views illustrating an example of a scenario where a scheme of the disclosure is implemented in a car.
Figure 11B:
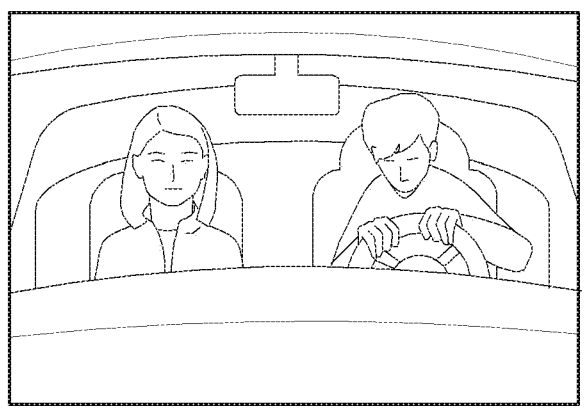

FIGS. 11A and 11B are views illustrating an example of a scenario where a scheme of the disclosure is implemented in a car.

FIG. 11A shows a hypothesis of being able to sense each user's state through a wearable device or camera and sensing a rise in the body temperature of one of several persons on board. The controlling apparatus may sense the current conditions of the people on board, calculate the calorific value for ones from whom a negative condition is shown, and control the set temperature and air blow direction and strength of the car air conditioner.

FIG. 11B shows a hypothesis in which each user's state may be sensed through a wearable device or camera and the driver is drowsy driving. The controlling apparatus may sense the driver's current condition (drowsy), calculate the calorific value for ones on board from whom a negative condition is shown, control the set temperature and air blow direction and strength of the car air conditioner, and visually/audibly output a notification message to keep the driver awaken.

Figure 12:
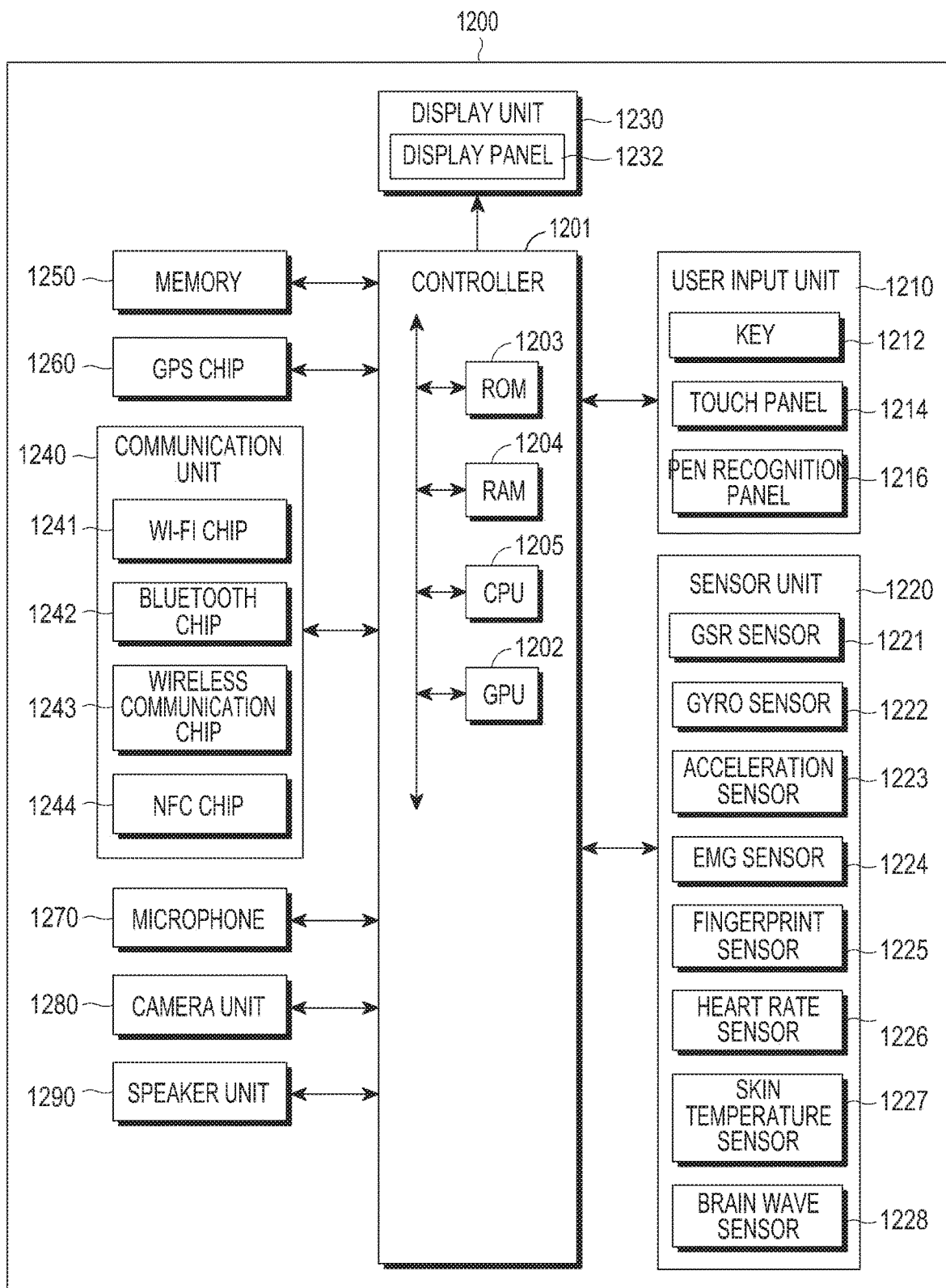
FIG. 12 is a view illustrating a configuration of a controlling apparatus (wearable device or smartphone) according to the disclosure.

FIG. 12 is a view illustrating a configuration of a control device (wearable device or smartphone) according to the disclosure.

The controlling apparatus 1200 may include a sensor unit 1220 measuring biometric signals, a controller 1201 controlling an equipment using the measured biometric signals, and a communication unit 1240 transmitting control commands to the equipment. The sensor unit 1220 may include at least one sensor. For example, the sensor unit 1220 may include a GSR sensor 1221 measuring the GSR, a gyro sensor 1222 measuring a change in direction of the controlling apparatus 1200, an acceleration sensor 1223 measuring the acceleration of a movement of the controlling apparatus 1200, an EEG sensor 1224 measuring a motion through the reaction of muscles to a nervous stimulus, a fingerprint sensor 1225 perceiving the user's fingerprint, a heart rate (PPG or ECG) sensor 1226 measuring the heart rate, a skin temperature sensor 1227, or a brain wave sensor 1228 measuring brain waves.

The controller 1201 may include at least one of a CPU 1205, a GPU 1202, a RAM 1203, and a ROM. All of the operations of the controlling apparatus described herein may be appreciated as being performed by the controller 1201. Although the controller 1201 and the communication unit 1240 are shown in separate modules for ease of description, the controller 1201 and the communication unit 1240 may be implemented in a single device.

The communication unit 1240 may include at least one of a Wi-Fi chip 1241 performing Wi-Fi communication, a bluetooth chip 1242 performing bluetooth communication, a wireless communication chip 1243 performing cellular communication, and an NFC chip performing NFC communication.

Selectively, the controlling apparatus 1201 may further include at least one of a display unit 1230, a memory 1250, a GPS chip 1260, a microphone 1270, a camera unit 1280, and a speaker unit 1290.

The display unit 1230 may include a display panel 1232 implemented as LEDs or an LCD. The display unit 1230 may output visual alarm messages to the user under the control of the controller 1201.

The memory 1250 may store biometric information obtained by the controller 1201, state information determined, calorific value calculated, and commands generated.

The microphone 1270 may be used to receive, e.g., sound information or voice information.

The camera unit 1280 may include an IR camera or a thermal imaging camera. The camera unit 1280 may be used to measure the external heat or movement of an object.

The speaker unit 1290 may output an audible alarm message to the user under the control of the controller 1201.

Figure 13:
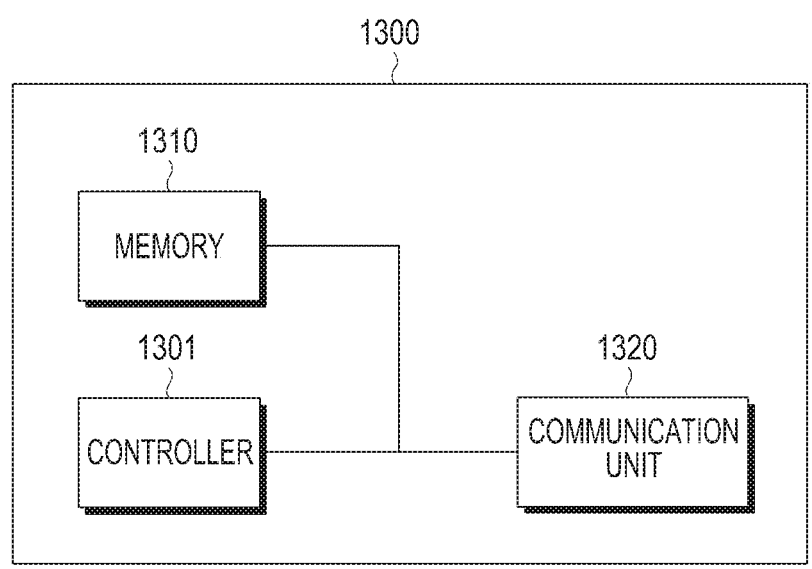
FIG. 13 is a view illustrating an example of a configuration where a controlling apparatus is a separate device, e.g., a home gateway or a cloud server according to the disclosure.

FIG. 13 is a view illustrating an example of a configuration where a controlling apparatus is a separate device, e.g., a home gateway or a cloud server according to the disclosure.

The controlling apparatus 1300 does not directly measure biometric signals but rather may receive biometric signals from the user's wearable device or ambient sensor. The controlling apparatus 1300 may include a controller 1301 controlling an equipment using the received biometric signals and a communication unit 1320 transmitting control commands to the equipment. All of the operations of the controlling apparatus described herein may be appreciated as being performed by the controller 1301. Although the controller 1301 and the communication unit 1320 are shown in separate modules for ease of description, the controller 1301 and the communication unit 1320 may be implemented in a single device.

The controlling apparatus 1300 may further include a memory 1310. The memory may store biometric information received from the communication unit 1320, state information determined by the controller 1401, calorific value calculated, and commands generated.

For example, the controller 1301 may control the communication unit 1320 to send a request for biometric information or user information to the wearable device or ambient sensor and receive the biometric information or user information from the wearable device or ambient sensor. The controller 1301 may also receive personal additional information (e.g., disease history) from an external server.

The controller 1301 may determine the user's state change, calculate the calorific value, or generate commands to control the equipment using the received information. The controller 1301 may control the communication unit 1320 to transfer the commands to the equipment.

It should be noted that the views of FIGS. 1 to 13 are not intended to limit the scope of the disclosure. In other words, all the components or operational steps illustrated in FIGS. 1 to 13 should not be construed as essential components to practice the disclosure, and the disclosure may be rather implemented with only some of the components without departing from the gist of the disclosure.

The above-described operations may be realized by equipping a memory device retaining their corresponding codes in an entity, function, server, wearable device, or any component of a terminal device in a communication system. That is, the controller in the entity, function, server, wearable device, or terminal device may execute the above-described operations by reading and running the program codes stored in the memory device by a processor or central processing unit (CPU).

As described herein, various components or modules in the entity, function, server, wearable device, or terminal device may be operated using a hardware circuit, e.g., a complementary metal oxide semiconductor-based logic circuit, firmware, software, and/or using a hardware circuit such as a combination of hardware, firmware, and/or software embedded in a machine-readable medium. As an example, various electric structures and methods may be executed using electric circuits such as transistors, logic gates, or ASICs.

Although specific embodiments of the disclosure have been described above, various changes may be made thereto without departing from the scope of the disclosure. Thus, the scope of the disclosure should not be limited to the above-described embodiments, and should rather be defined by the following claims and equivalents thereof.

What is claimed is:

1. A method for controlling at least one external device based on biometric information by an electronic device, the method comprising:
   obtaining first biometric information;
   obtaining first state information related to a body state based on the obtained first biometric information and second biometric information stored in a memory of the electronic device;
   obtaining second state information related to emotional state based on the first biometric information;
   selecting the at least one external device from a plurality of external devices based on the first state information and the second state information;
   generating a command for controlling the at least one external device based on the first state information and the second state information; and
   transmitting the command to the at least one external device.

2. The method of claim 1, further comprising:
obtaining a variation ratio of the first biometric information using the second biometric information; and
identifying whether to control the at least one external device based on the second state information and the variation ratio.

3. The method of claim 2, wherein the obtaining of the first state information based on the first biometric information and the second biometric information further comprises:
when the variation ratio is greater than or equal to a reference value, obtaining the first state information.

4. The method of claim 1, wherein the obtaining of the first state information based on the first biometric information and the second biometric information further comprises:
in response to identifying a user's emotional change based on the second state information, obtaining the first state information.

5. The method of claim 1,
wherein the generating of the command for control the at least one external device comprises:
obtaining an apparent temperature using the first state information, and
generating the command based on the apparent temperature,
wherein the apparent temperature is a predicted mean vote (PMV), and
wherein the command is generated when the PMV is not within a predetermined range.

6. The method of claim 1, further comprising:
obtaining third biometric information after transmitting the command to the external device;
identifying whether a user's emotional state has changed based on the third biometric information;
when identifying that the user's emotional state has changed, generating an additional command based to the third biometric information; and
transmitting the additional command to the at least one external device.

7. The method of claim 6, wherein the identifying of whether a user's emotional state has changed based on the third biometric information comprises:
obtaining a variation ratio of the third biometric information using the second biometric information, and
identifying a change of a user's emotional based on the variation ratio of the third biometric information and the second state information.

8. The method of claim 1,
wherein the second state information includes information of a plurality of emotional states, and
wherein each of the information of the plurality of emotional states includes different variation value based on at least one piece of biometric information.

9. An electronic device comprising:
a memory;
a communication circuit; and
at least one processor;
wherein the at least one processor is configured to:
obtain first biometric information,
obtain first state information related to a body state based on the first biometric information and second biometric information stored in the memory,
obtain second state information related to emotional state based on the first biometric information,
determine at least one external device from a plurality of external devices based on the first state information and the second state information,
generate a command for control the at least one external device based on the first state information and the second state information, and
transmit the command via the communication circuit to the at least one external device.

10. The electronic device of claim 9,
wherein the at least one processor is further configured to:
obtain a variation ratio of the first biometric information using the second biometric information, and
identify whether to control the at least one external device based on the second state information and the variation ratio, and
wherein the first state information is obtained when the variation ratio is greater than or equal to a reference value.

11. The electronic device of claim 9, wherein the at least one processor is further configured to obtain the first state information in response to identifying a user's emotional change based on the second state information.

12. The electronic device of claim 9,
wherein the at least one processor is further configured to obtain a-an apparent temperature using the first state information,
wherein the apparent temperature is a predicted mean vote (PMV), and
wherein the command is generated when the PMV is not within a predetermined range.

13. The electronic device of claim 9, wherein the at least one processor is further configured to:
obtain third biometric information after transmitting the command to the external device
obtain a variation ratio of the third biometric information using the second biometric information,
identify whether a user's emotional state has changed based on the variation ratio of the third biometric information and the second state information,
when indcntifying identifying that the user's emotional state has changed, generate an additional command based to the third biometric information and
transmit the additional command to the at least one external device.

14. The electronic device of claim 9,
wherein the second state information includes information of a plurality of emotional states, and
wherein each of the information of the plurality of emotional states includes different variation value based on at least one piece of biometric information.

15. The electronic device of claim 9, wherein the first biometric information includes at least one of heart rate, pulse transmit time, breathing time, skin temperature, galvanic skin response, brain wave on frontal lube, or brain wave on parietal lobe.

* * * * *